United States Patent
Otto

(10) Patent No.: US 6,857,137 B2
(45) Date of Patent: Feb. 22, 2005

(54) URINE COLLECTION DEVICE

(75) Inventor: Edgar Allan Otto, Boca Raton, FL (US)

(73) Assignee: Edgar A. Otto, Boca Raton, FL (US)

( * ) Notice: Subject to any disclaimer, the term of this patent is extended or adjusted under 35 U.S.C. 154(b) by 21 days.

(21) Appl. No.: 10/401,260

(22) Filed: Mar. 27, 2003

(65) Prior Publication Data

US 2004/0187199 A1 Sep. 30, 2004

(51) Int. Cl.$^7$ ............................................. A47K 11/12
(52) U.S. Cl. ........................................ 4/144.1; 604/349
(58) Field of Search ........................... 604/144.1–144.4, 604/347, 349, 350

(56) References Cited

U.S. PATENT DOCUMENTS

| | | | |
|---|---|---|---|
| 2,749,558 A | 6/1956 | Lent et al. | |
| 3,626,941 A | 12/1971 | Webb | |
| 3,776,231 A | * 12/1973 | Holbrook et al. | ............ 604/322 |
| 4,298,006 A | * 11/1981 | Parks | ............................ 607/106 |
| 4,683,598 A | * 8/1987 | Jones | ................................ 4/301 |
| 4,747,166 A | 5/1988 | Kuntz | |
| 5,176,667 A | * 1/1993 | DeBring | ..................... 604/356 |
| 5,269,030 A | 12/1993 | Pahno et al. | |
| 5,449,347 A | 9/1995 | Preen et al. | |
| 5,466,229 A | 11/1995 | Elson et al. | |
| 5,496,300 A | * 3/1996 | Hirsch et al. | ................ 604/327 |
| 5,551,097 A | 9/1996 | Short | |
| 5,681,297 A | 10/1997 | Hashimoto et al. | |
| 5,701,612 A | 12/1997 | Daneshvar | |
| 5,809,586 A | 9/1998 | Kitamura | |
| 5,842,237 A | 12/1998 | Hargest et al. | |
| 6,001,086 A | 12/1999 | Rammacher | |
| 6,009,570 A | 1/2000 | Hargest et al. | |
| 6,110,159 A | 8/2000 | Tsujita et al. | |
| 6,238,378 B1 | 5/2001 | Perez | |
| 6,311,339 B1 | * 11/2001 | Kraus | ......................... 4/144.3 |

* cited by examiner

Primary Examiner—Charles E. Phillips
(74) Attorney, Agent, or Firm—J. Rodman Steele, Jr.; Michael K. Dixon; Akerman Senterfitt

(57) ABSTRACT

A portable urine collection device having a closed loop system that is easily usable by a patient. The urine collection device includes a urine collection receptacle for receiving a fluid from a patient. The urine collection receptacle may be coupled to a reservoir with a conduit. The reservoir may be a disposable plastic bag having markings for determining the amount of urine contained in the bag. The urine collection receptacle may have multiple configurations and may be configured to receive urine from a female or male human being, or both. The urine collection device may also include a pump for pumping urine from the urine collection receptacle to the reservoir without components of the pump contacting the urine being pumped.

21 Claims, 2 Drawing Sheets

URINE COLLECTION DEVICE

FIELD OF THE INVENTION

This invention is directed generally to urine collection devices, and more particularly, to portable urine collection devices for collecting urine from incapacitated patients who are unable to use conventional facilities.

BACKGROUND

Removal of urine from incapacitated humans has been undertaken using a variety of devices and methods with mixed amounts of success. For instance, diapers have been used to remove urine from patients. While diapers collect most of the urine produced by a patient, diapers leak, which can cause rashes on patients. In addition, diapers must be changed to function adequately. Otherwise, urine may leak from the diaper. For at least these reasons, diapers are not the most desirable choice of devices for collecting urine from a patient.

Another device commonly used to collect urine from incapacitated patients who are unable to use conventional toilets is a bedpan. Bedpans have been used successfully but produce undesirable odors and are, at times, unsightly. In addition, bedpans often require the assistance of a nurse to use. While a nurse is respectful of a patient's privacy, nurses often make patients uncomfortable. Use of bedpans is also limited to use with beds that are adapted for their use. Thus, bedpans are not portable and are not capable of being used in a variety of locations.

Catheters are also commonly used to remove urine from men. Catheters are typically composed of small diameter tubing that is placed inside the urethra of a patient. While catheters are efficient at removing urine from men, catheters often causes a high amount of infection. Thus, a need exists for removing urine from men without causing infection.

Still another class of devices that has been developed more recently are urine suction devices. Urine suction devices transport urine from a patient to a collection device using pumps, gravity and other forces. For instance, U.S. Pat. No. 6,311,339 is directed to a suction collector that receives urine in a well through a flexible urine collection conduit. The suction collector includes a vacuum for transporting urine from a patient to a well. The suction collector is operable once a urine collection receptacle is sealed against a patient's skin surface and the pump is actuated. While the suction collector has overcome some of the disadvantages of the diaper and the bedpan, the suction collector is not without its inconveniences.

Thus, a need exists for a portable urine collector that is easy to use by incapacitated patients.

SUMMARY OF THE INVENTION

This invention is a urine collection device for collecting urine from patients who may be incapacitated and unable to used conventional toilets. The urine collection device may include a urine collection receptacle configured to receive urine from a patient. The urine collection device may be configured differently for male and female users. The urine collection receptacle may be coupled to a reservoir using a conduit. A check valve may be positioned along the conduit proximate to the collection receptacle to preventing urine from flowing back into the collection receptacle. The reservoir may be portable and releasably coupled to the conduit between the urine collection receptacle and the reservoir. The urine collection device may also include a pump coupled to the conduit for pumping urine from the urine collection receptacle to the reservoir. The pump may be capable of pumping urine without contacting the urine while the pump is in contact with a portion of the conduit between the urine collection receptacle and the reservoir. In one embodiment, the pump is a peristaltic pump.

The urine collection device may include a stand for supporting the reservoir, the pump, and the conduit. The stand may be portable and include a plurality of wheels for moving the stand. The stand may include a container that is releasably coupled to the stand for supporting the reservoir. The stand may also include a towelette dispenser for storing sanitary cleansing products.

The urine collection device may include support device for supporting the urine collection receptacle when the urine collection receptacle is not in use. An on/off switch may be coupled to the support device for controlling the pump. The on/off switch may be configured so that the pump is turned on when the urine collection receptacle is removed from the support device, and the pump is turned off when the urine collection receptacle is hung on the support device.

An advantage of this invention is that the urine collection device is portable and enables patients to urinate in any location with comfort and without the assistance of a nurse.

Another advantage of this invention is that the urine collection device is operable by simply lifting a urine collection receptacle from a support device and urinating in the urine collection receptacle.

Yet another advantage of this invention is that the urine collection device is a closed system wherein every portion of the urine collection device that contacts urine may be easily removed from the device and disposed. Thus, this system is easy to clean.

Still another advantage of this invention is that the reservoir is marked to indicate the volume of urine contained in the reservoir for analytical purposes.

Another advantage of this invention is that the urine collection device includes a unisex version of the urine collection receptacle.

Yet another advantage of this invention is that the urine collection device prevents urine from flowing backwards through the conduit back into the urine collection receptacle after urine has entered the conduit.

These and other features and advantages of the present invention will become apparent after review of the following drawings and detailed description of the disclosed embodiments.

BRIEF DESCRIPTION OF THE DRAWINGS

The accompanying drawings, which are incorporated in and form a part of the specification, illustrate embodiments of the presently disclosed invention and, together with the description, disclose the principles of the invention.

DETAILED DESCRIPTION OF THE INVENTION

Figure 1:
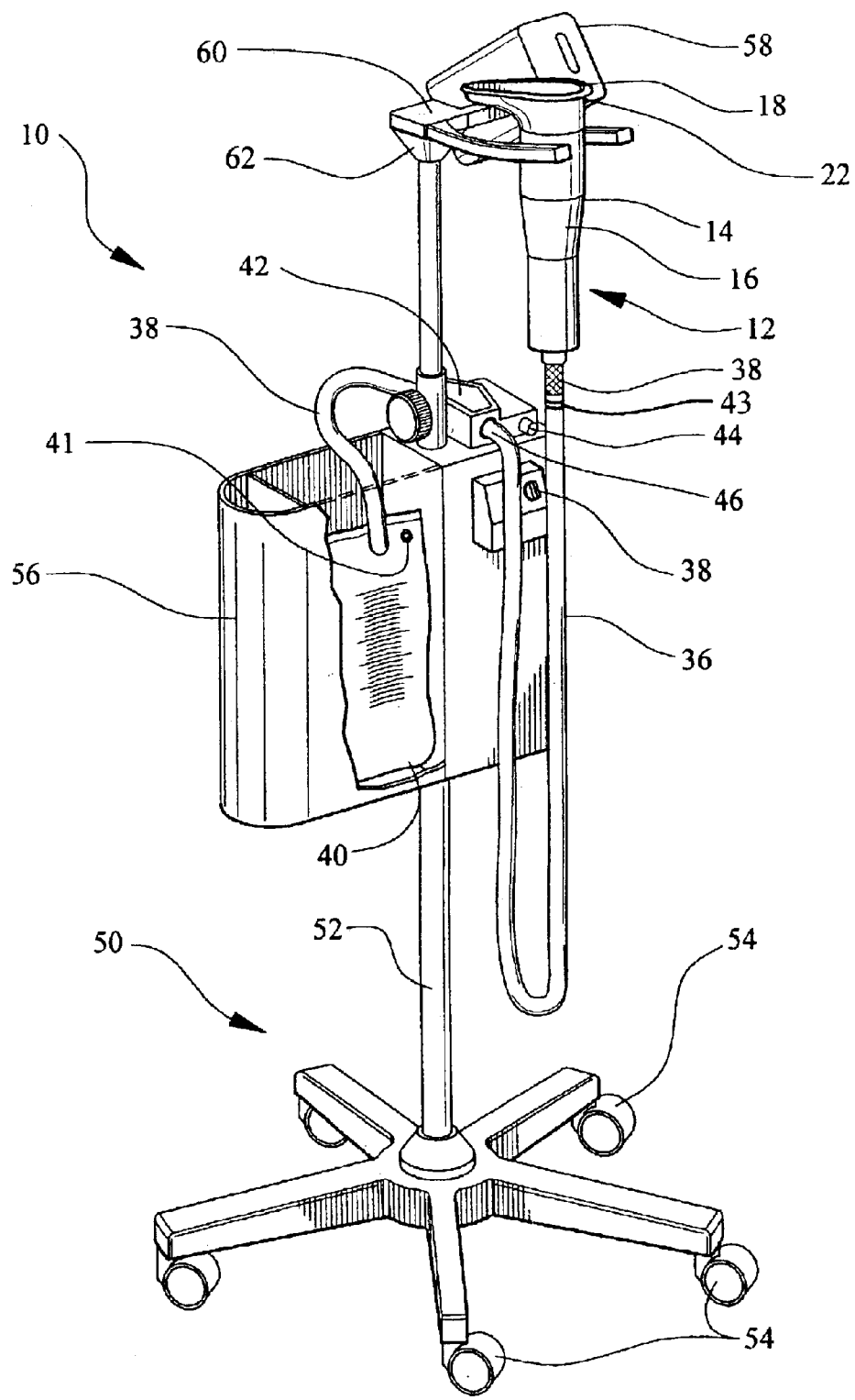
FIG. 1 is a perspective view of an exemplary embodiment of a urine collection device.

As shown in FIG. 1, this invention is a urine collection device 10 for collecting urine from patients. Urine collection device 10 may be used to collect urine from humans and animals alike. More specifically, urine collection device 10 may be used to collect urine from bedridden patients, patients who are incapacitated and unable to use conventional toilets, and others. Urine collection device 10 may also be used to collect urine from patients in various positions, such as, but not limited to, a seated position, a standing position, a prostrate position, and other positions.

In one embodiment, urine collection device 10 includes one or more urine collection receptacles 12 for receiving urine from a patient. Urine collection receptacle 12 is configured so that a patient may urinate into the urine collection receptacle 12 without assistance from a nurse or other assistant. Urine collection receptacle 12 may be configured in male and female versions or in a unisex version configured to be used by both sexes. A male version 14, as shown in FIG. 1, may be a cylinder 16 have an opening 18 configured to receive a male human penis. Opening 18 may include a flexible perimeter 22 coupled to opening 18 to decrease the risk of injury to a patient caused by use of the urine collection receptacle. Male version 14 is not limited to the configuration shown in FIG. 1. Instead, male version 14 may have configurations other than the embodiment shown.

Figure 2:
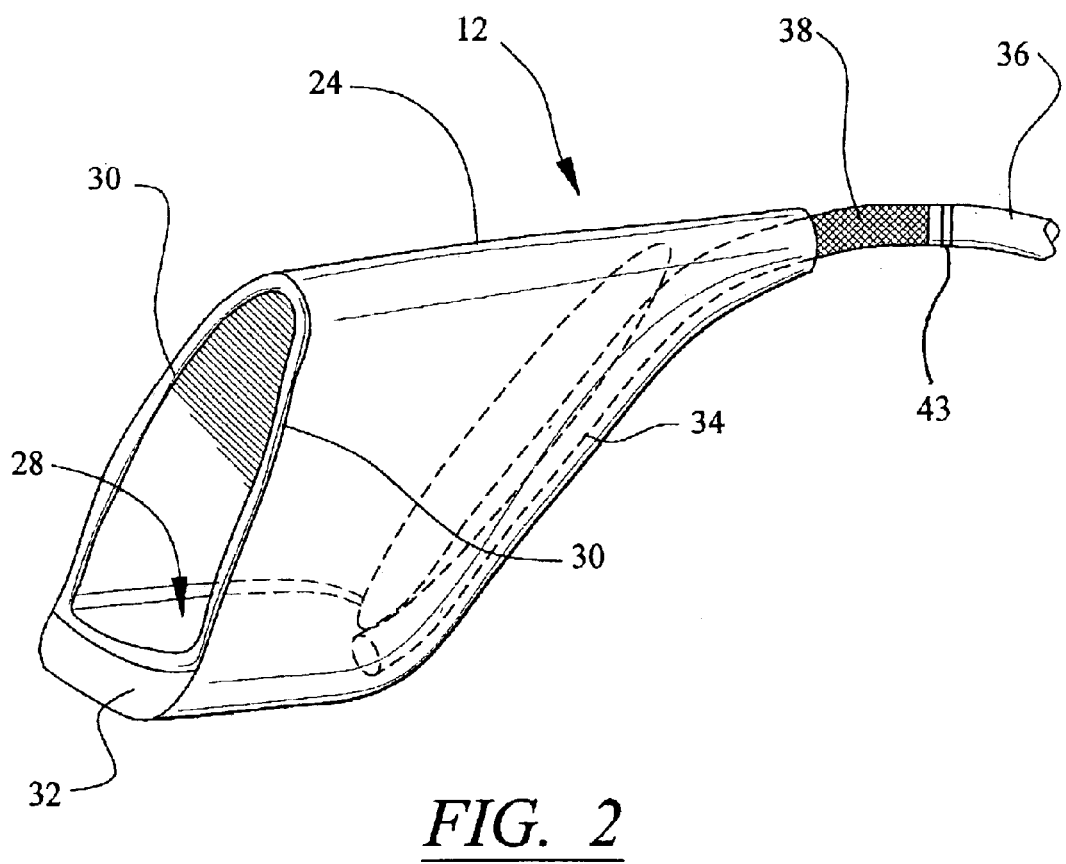
FIG. 2 is a perspective view of unisex version of a urine collection receptacle.

A unisex version 24 of the urine collection receptacle 12, as shown in FIG. 2, is configured to receive urine from a female human being without significant spillage. Unisex version 24 conforms to a skin surface of a female human being proximate to a urethra so that urine expelled from the urethra collects in urine collection receptacle 12. The unisex version 24 includes a collection basin 28 that is configured to collect urine. Collection basin 28 is formed by sides 30 and lip 32. Sides 30 are configured to fit between legs of a female or male patient. A tube 34 is positioned in the urine collection receptacle 12 to draw urine from collection basin 28.

In one embodiment, urine collection receptacle 12 is releasably coupled to a conduit 36 using, for instance, a quick connect fitting 38. Use of quick connect device 38 enables male version 14 and unisex version 24 of urine collection receptacle 12 to be interchanged with ease. Urine collection receptacle may also be attached to conduit 38 using devices other than quick connect fitting 38. For instance, urine collection receptacle 12 may be coupled to conduit 36 using one or more adhesives, mechanical connectors, and other coupling devices.

Urine collection receptacle 12 is coupled to a reservoir 40 using conduit 36. Conduit 36 may be made from rigid or flexible materials. In one embodiment, conduit 36 is a flexible tubing that is transparent so that the flow of urine through the tubing to reservoir 40 can be monitored. Conduit 36 may also be opaque and formed from any color. Reservoir 40 may be formed from any device capable of holding urine. In one embodiment, reservoir 40 is a transparent, flexible, plastic bag that is marked to indicate the amount of fluid contained in reservoir 40. In other embodiments, reservoir 40 may be a tank, a laboratory container, or other such device. Reservoir 40 may also include an exhaust valve 41 for releasing gases from reservoir 40. Reservoir 40 may be releasably coupled to conduit 36 using, for instance, quick connect fitting 38. By releasably coupling reservoir 40 to conduit 36, reservoir 40 may be easily removed and replaced. In other embodiments, reservoir 40 may be permanently attached to conduit 36 using one or more adhesives, mechanical connectors, and other coupling devices.

Urine collection device 10 may include one or more check valves 43 for preventing urine from flowing out of conduit 36 and into urine collection receptacle 12. In at least one embodiment, check valve 43 may be positioned in conduit 36 adjacent to urine collection receptacle 21, as shown in FIG. 1. Alternatively, check valve 43 may be coupled directly to urine collection receptacle 12 or positioned at other locations along conduit 36. Check valve 43 may prevent urine from spilling out of conduit 36 and onto a patient after the patient has finished using urine collection device 10.

Urine collection device 10 may also include a pump 42 for moving urine from the urine collection filter 12 to reservoir 40. Pump 42 preferably transports urine from the urine collection filter 12 to reservoir 40 through conduit 36 without components of the pump contacting the urine. In one embodiment, pump 42 is a peristaltic pump that allows conduit 36 to be placed in contact with pump 42 without urine contacting components of pump 42. More specifically, conduit 36 is placed in pump 42 by moving a lever 44, which in turn opens a cavity 46 for receiving conduit 36. Conduit 36 is placed in cavity 46 and lever 44 is rotated to secure conduit 36 in pump 42. Pump 42 draws urine from urine collection receptacle 12 and deposits the urine in reservoir 40. Pump 42 may be operated at varying speeds and may be controlled using a dial 48 or other device. Pump 42 may be powered by batteries, which may or may not be rechargeable, or with an alternating current (AC) power source such as power that is typically available from a public utility and supplied through a wall outlet.

Urine collection device 10 may include a stand 50 for supporting pump 42, reservoir 40, and urine collection receptacle 12. Stand 50 may include a center support shaft 52 coupled to a plurality of wheels 54. Wheels 54 may include, but are not limited to, caster wheels. Pump 42 may be releasably coupled to shaft 52 so that the height of pump 42 and reservoir 40 can be adjusted. Stand 50 may also include a container 56 coupled to stand 50 for supporting reservoir 40. Stand 50 may have a bottom and may or may not have side walls. Stand 50 preferably is light weight and easily transportable. Stand 50 may also include a towelette dispenser 58. Towelette dispenser 58 may be releasably attached to stand 50 and may be configured to receive a conventional tissue box.

Urine collection device 10 may also include a support device 60 that is configured to support urine collection receptacle 12 when urine collection receptacle is not in use. In one embodiment, support device 60 includes two or more prongs capable of receiving urine collection receptacle 12. In another embodiment, support device 60 may include a plate having a hole capable of receiving the urine collection receptacle 12. The hole is sized to receive the urine collection receptacle 12 but is not larger than the width of the urine collection receptacle 12.

Urine collection device 10 may include an on/off switch 62 for actuating pump 42. In one embodiment, on/off switch 62 is actuated by moving support device 60. Support device 60 may be configured so that on/off switch 62 is closed when urine collection receptacle 12 is removed from support device 60. Closing on/off switch 62 activates pump 42. Conversely, on/off switch 62 is opened and pump 42 is shut off when urine collection receptacle 12 is placed back on support device 60.

Urine collection device 10 is configured to be operated by a patient but may also be operated by an assistant, such as a nurse, to remove urine from a patient. Urine collection device 10 should be checked before use to ensure that a proper urine collection receptacle 12, either male version 14, a female version, or unisex version 24, is attached. If urine collection receptacle 12 needs to be changed, urine collection receptacle 12 may be changed by disconnecting quick connect fitting 38 and connecting the appropriate urine collection receptacle 12.

A patient may activate urine collection device 10 by removing urine collection receptacle 12 from support device 60. Urine collection receptacle 12 should be placed proximate to the patient's urethra to capture urine as the urine is expelled from the urethra. Once the patient begins to urinate, urine is collected in urine collection receptacle 12. Pump 42 draws urine from urine collection receptacle 12 and pumps the urine into reservoir 40. After the patient has finished urinating, urine collection receptacle 12 is placed on support device 60, which turns pump 42 off. The urine collected in reservoir 40 may be emptied from reservoir 40 or reservoir 40 may be disconnected from conduit 36 at quick connect fitting 38 and disposed. A replacement reservoir 40 may be coupled to quick disconnect fitting 38.

The foregoing is provided for purposes of illustrating, explaining, and describing embodiments of this invention. Modifications and adaptations to these embodiments will be apparent to those skilled in the art and may be made without departing from the scope or spirit of this invention.

I claim:

1. A urine collection device, comprising;
   a urine collection receptacle configured to receive urine from a patient;
   a reservoir for collecting the urine received by the urine collection receptacle, wherein the reservoir is portable and is in fluid communication with the urine collection receptacle trough a conduit;
   a pump capable of pumping a fluid without contacting the fluid, wherein the pump is in contact with a portion of the conduit between the urine collection receptacle and the reservoir for pumping urine from the urine collection receptacle to the reservoir; and
   an on/off switch coupled to a support device for supporting the urine collection receptacle when the urine collection receptacle is not in use and configured to turn the pump on when the urine collection receptacle is removed from the support device.

2. The urine collection device of claim 1, further comprising a portable frame for supporting the urine collection device.

3. The urine collection device of claim 2, wherein the portable frame further comprises a plurality of wheels coupled to the frame.

4. The urine collection device of claim 2, wherein the portable frame further comprises a container for holding cleaning products.

5. The urine collection device of claim 1, wherein the urine collection receptacle is releasable coupled to the conduit using a quick release fitting.

6. The urine collection device of claim 1, wherein the urine collection receptacle is a cylinder having an opening configured to receive a male human penis.

7. The urine collection device of claim 1, wherein the urine collection receptacle conforms to a skin surface of a female human proximate to a urethra so that urine flowing through the urethra and out of the female human collects in the urine collection receptacle.

8. The urine collection device of claim 7, wherein the urine collection receptacle further comprises a collection basin for collecting urine to be pumped to the reservoir.

9. The urine collection device of claim 1, further comprising a check valve coupled to the urine collection receptacle.

10. The urine collection device of claim 1, wherein the pump is a peristaltic pump.

11. The urine collection device of claim 1, wherein the conduit is a flexible conduit.

12. The urine collection device of claim 11, wherein the conduit is transparent.

13. The urine collection device of claim 1, wherein the reservoir is connected to the conduit with a quick release fitting.

14. The urine collection device of claim 1, wherein the reservoir is transparent and marked to indicate the volume of urine contained in the reservoir.

15. The urine collection device of claim 1, wherein the reservoir includes an exhaust port.

16. The urine collection device of claim 1, wherein the reservoir is a tank.

17. The urine collection device of claim 1, wherein the pump is operable at varying speeds.

18. The urine collection device of claim 1, further comprising a check valve.

19. A urine collection device, comprising:
   a urine collection receptacle configured to receive urine from a patient;
   reservoir for collecting the urine received by the urine collection receptacle, wherein the reservoir is portable and is in fluid communication with the urine collection receptacle through a flexible conduit;
   a peristaltic pump capable of pumping a fluid without contacting the fluid, wherein the peristaltic pump is in contact with a portion of the conduit between the urine collection receptacle and the reservoir for pumping urine from the urine collection receptacle to the reservoir; and
   an on/off switch coupled to a support device for supporting the urine collection receptacle when the urine collection receptacle is not in use and configured to turn the pump on when the urine collection receptacle is removed from the support device.

20. A urine collection device, comprising:
   a portable stand having a plurality of wheels;
   a urine collection receptacle configured to receive urine from a patient;
   a check valve coupled to the urine collection receptacle;
   a reservoir for collecting the urine received by the urine collection receptacle, wherein the reservoir is portable and is in fluid communication with the urine collection receptacle through a conduit;
   a pump releasably coupled to the portable stand and capable of pumping a fluid without contacting the fluid, wherein the pump is in contact with a portion of the conduit between the urine collection receptacle and the reservoir for pumping urine from the urine collection receptacle to the reservoir;
   a support device coupled to the portable stand and configured to support the urine collection receptacle when the urine collection receptacle is not in use; and
   an on/off switch coupled to a support device and configured to turn the pump on when the urine collection receptacle is removed from the support device and to turn the pump off when the urine collection receptacle is supported by the support device.

21. The urine collection device of claim 20, wherein the pump is a peristaltic pump.

* * * * *